(12) United States Patent
van Geel et al.

(10) Patent No.: US 8,741,274 B2
(45) Date of Patent: Jun. 3, 2014

(54) ACRYLIC POLYMER

(75) Inventors: Jos van Geel, Vught (NL); Dirk Weber, Basel (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/503,768

(22) PCT Filed: Oct. 19, 2010

(86) PCT No.: PCT/EP2010/065744
§ 371 (c)(1),
(2), (4) Date: Apr. 24, 2012

(87) PCT Pub. No.: WO2011/057882
PCT Pub. Date: May 19, 2011

(65) Prior Publication Data
US 2012/0207696 A1    Aug. 16, 2012

(30) Foreign Application Priority Data
Nov. 16, 2009  (EP) .................................... 09176064

(51) Int. Cl.
*A61K 8/81*  (2006.01)
*A61Q 5/06*  (2006.01)

(52) U.S. Cl.
USPC ...................................................... 424/70.16

(58) Field of Classification Search
None
See application file for complete search history.

(56) References Cited

FOREIGN PATENT DOCUMENTS

GB      1312098      4/1973

OTHER PUBLICATIONS

International Search Report for PCT/SE2010/065744 mailed Nov. 19, 2010.
Written Opinion of the International Searching Authority mailed Nov. 19, 2010.

*Primary Examiner* — Paul Dickinson
(74) *Attorney, Agent, or Firm* — Nixon & Vanderhye P.C.

(57) ABSTRACT

The present invention relates to acrylic polymer beads having very low residual monomer content as well as to their use in hair care preparations in particular as styling agent.

16 Claims, No Drawings

ACRYLIC POLYMER

This application is the U.S. national phase of International Application No. PCT/EP2010/065744 filed 19 Oct. 2010 which designated the U.S. and claims priority to EP 09176064.5 filed 16 Nov. 2009, the entire contents of each of which are hereby incorporated by reference.

The present invention relates to acrylic polymer beads having very low residual monomer content as well as to their use in hair care preparations in particular as styling agent.

Acrylate Copolymers such as e.g. Luvimer® (BASF), Balance® (Akzo Nobel) or Acudyne® (Rohm und Haas) are widely used in the Hair Care Industry as setting polymers for Aerosol and non-Aerosol Sprays. These polymers are prepared with emulsion polymerization technology which allows a good control over critical polymer parameters like molecular weight, particle size in the nm range (typically 50-300 nm) and residual monomer content. However, no micron sized particles are obtained during emulsion polymerisation. Due to the small particle size dried emulsion polymers have a much larger dusting tendency compared to dried polymer beads obtainable by suspension polymerization. On the other hand polymer emulsions used as such to avoid the dusting issue need to be preserved to prevent bacterial or fungal growth.

The problem of dustiness of dried emulsion polymers can be overcome by bead-type suspension polymerization which is a well known method of polymerization in which the polymer formed is obtained as micron sized spherical beads or pearls. However, even though the water soluble by-products may be removed with the stationary water phase during the final de-watering and washing cycle the water insoluble by-products such as in particular the unreacted monomers stay within the polymer beads and lead to characteristic off odours, lowered glass transition temperatures ($T_g$) and toxicological issues, especially when the monomers are taken from acrylic acid/methacrylic acid and theirs esters.

Thus, even though acrylic polymer beads are widely applied in the field of colorants, photographic applications, inks, or plastics the application in personal care products such as in particular hair care preparations is still limited due to toxicological issues resulting from the residual monomer content.

Therefore, there is an ongoing need for a process for the preparation of acrylic polymer beads for cosmetic applications, in particular for hair care preparations with a very low residual monomer content such as below 250 ppm and in particular below 100 ppm.

Furthermore, such acrylic polymer beads need to have a sufficiently high $T_g$, of at least 45° C. and in particular between 80-120° C. in order to prevent the beads from sticking together during processing and storage. In order to be industrially viable the beads should be obtainable by an efficient and economical attractive process without the necessity of applying elaborate purification processes in order to achieve the low monomer content. Furthermore, the beads should be preservative-free, non dusty, free-flowing, and exhibit easy solubilisation and no lumping even without the addition of separating agents.

In addition the acrylic polymer beads should be compatible with the customary cosmetic ingredients and readily formulated as pump or aerosol spray in solvents or solvent mixtures. The acrylic polymer beads applied to the hair should dry rapidly and impart good setting and prolonged hold to the hair (such as e.g. good curl retention) even at increased atmospheric humidity and have a good ability to be washed out. In addition, the treated hair should have good haptic properties such as, for example, a good feel to the touch and being non-sticky.

Surprisingly, it has been found that the residual monomer content of acrylic polymer beads obtainable by suspension polymerisation of a mixture of methacrylic acid, n-butyl methacrylate and ethylacrylate can be significantly lowered by the addition of ethyl methacrylate.

Thus, the invention relates in a first embodiment to a process for the preparation of acrylic polymers beads comprising subjecting a monomer composition consisting of a mixture of methacrylic acid (MAA), n-butyl methacrylate (BMA), ethylacrylate (EA) and ethyl methacrylate (EMA) to suspension polymerization.

By the term "polymer beads" in connection with the present invention is meant polymer particles that are simple to isolate e.g. by filtering or centrifuging. The polymer beads in connection with the present invention typically have an average diameter of at least 50 μm, preferably at least 150 μm. Generally, the beads have a diameter between 50 and 1500 μm such as in particular between 150 to 400 μm.

In a particular embodiment the monomer composition consists of a mixture of 10-30 wt.-% of methacrylic acid, 35-65 wt.-% of n-butyl methacrylate, 5-15 wt.-% of ethyl acrylate and 10-35 wt-% of ethyl methacrylate such as in particular of 15-25 wt.-% of methacrylic acid, 38-60 wt.-% of n-butyl methacrylate, 8-15 wt.-% of ethyl acrylate and 15-25 wt.-% of ethyl methacrylate such as even more in particular of 17-22 wt.-% of methacrylic acid, 44-56 wt.-% of n-butyl methacrylate, 9-15 wt.-% of ethyl acrylate and 15-25 wt.-% of ethyl methacrylate.

Particular low monomer contents are obtained using monomer mixtures consisting of 15-22 wt.-% of methacrylic acid, 44-56 wt.-% of n-butyl methacrylate, 9-15 wt.-% of ethyl acrylate and 18-22 wt.-% of ethyl methacrylate.

The term 'consisting of' as used according to the present invention means that the total amount of monomer ideally sum up to 100 wt.-%. It is however not excluded that small amount of impurities or additives may be present such as e.g. in amounts of less than 5 wt.-%, preferably less than 3 wt.-% which are e.g. introduced via the respective raw materials.

Preferably the ratio of ethyl methacrylate (EMA) to ethyl acrylate (EA) (w/w) in the monomer compositions according to the invention and outlined above is selected in the range of 4:1 to 1:1, preferably in the range of 2:1 to 1:1, in particular in the range of 2:1 to 1.3:1.0, which can also be expressed as coefficient of EMA/EA which accordingly should preferably be selected in the range of 4 to 1, preferably in the range of 2 to 1 such as in particular in the range of about 2.0 to 1.3.

It is further preferred that the amount of methacrylic acid used in the monomer compositions according to the invention is less than 25 wt.-%, such as about 15 to 22 wt.-%, in particular about 17 to 22 wt.-% and even more in particular about 20 wt.-% based on the total amount of the monomers in order to further reduce the residual monomer content.

Particular preferred are monomer compositions wherein the MAA content is selected in the range of about 15-22 wt.-%, in particular 17 to 22 wt.-% and the coefficient of EMA/EA is selected in the range of about 2.0 to 1.3 as such polymer exhibit a good solubility in water or alcohols as well as mixtures thereof while having an extremely low residual monomer content.

In another embodiment, the invention relates to acrylic polymer beads obtainable by the process according to the invention. In particular the to acrylic polymer beads according to the invention have a residual monomer content of less than 250 ppm such as in particular of less than 100 ppm.

The acrylic polymer beads according to the invention are prepared by suspension polymerization (also known as granular, bead, or pearl polymerization due to the shape of the resultant polymer particles) according to known methods in the art as illustrated in the examples.

Initiators for polymerizing the monomers to provide the acrylic polymer beads of the invention are those which are normally suitable for free-radical polymerization of acrylate monomers and which are oil-soluble and have low solubility in water such as e.g. organic peroxides, organic peroxyesters and organic azo initators. The initiator is generally used in an amount of about 0.01 to 1 wt.-% based on the total monomer content.

Useful chain transfer agents include mercaptans, carbon tetrabromide, and mixtures thereof. Dodecylmercaptane is preferred. The chain transfer agent generally is used in an amount of about 0.01 to 1.0 wt.-%, preferably in an amount of 0.01 to 0.5 wt.-% based on the total monomer content.

Optionally, a water soluble inhibitor can be added to inhibit polymerization in the water phase in order to prevent the formation of too much polymer by emulsion and/or solution polymerization in the water phase, which can result in bead agglomeration or emulsion type polymerization. Suitable inhibitors include those selected from thiosulfates, thiocyanates, water soluble hydroquinones and nitrites. When used, the water soluble inhibitor can generally be added in an amount of from about 0.01 to about 1 parts by weight based on 100 parts total monomer content.

Furthermore, a water soluble or water dispersible polymeric stabilizer is needed to stabilize the suspension and in order to obtain stable beads. The stabilizer is preferably a synthetic water soluble or water dispersible polymer such as e.g. polyvinylalcohol, gelatine, starch, methylcellulose, carboxymethylcellulose, hydroxyethylcellulose, poly(meth) acrylic acid and their sodium salts, and the like. The stabilizer is preferably used in an amount of about 0.001 to 10 wt.-%, more preferable in an amount of about 0.01 to 1 wt-% based on the total monomer content.

Other additives can optionally be used such as e.g. mono-, di- and trivalent metal salts, borax, urea, glyoxal and urea formaldehyde resin. Biocides (both bactericides and fungicides) can also be added, in order to prevent microbial growth in the finished product and during its use.

The monomers, free-radical initiator, and any optional materials can be mixed together in the prescribed ratio to form a premix. The stabilizer can be combined with water and then with the premix to form an oil in water suspension. The resulting suspension typically comprises from about 10 to about 50 weight percent monomer premix and from about 90 to about 50 weight percent water phase. Bead-type suspension polymerization in accordance with the present invention is typically a thermally initiated polymerization and is preferably carried out with agitation for about 2 to about 16 hours at a temperature between about 40° C. and 90° C. After isolation of the beads according to standard methods such as filtration or centrifugation the beads are preferably subjected to an extended drying, preferably at about 40-100° C. and more preferably at about 80-100° C. in order to further reduce the residual monomer content to an amount of below 250 ppm such as in particular below 100 ppm. The drying can be performed by commonly known means to a person skilled in the art such as e.g. using a fluidized bed dryer or a conventional oven. The drying time can be easily adjusted by a person skilled in the art and is usually carried out over a period of 3 to 40 h such as about 8 to 20 h and in particular about 8 to 10 h.

Thus, in a further embodiment the invention relates to the process according to the invention said process further comprising the isolation of the beads followed by an extended drying step at 40 to 100° C. such as in particular at 80-100° C. Preferably the drying step is carried out over a period of 3 to 40 h, more in particular of 8 to 20 h such as e.g. of 8 to 10 h.

The acrylic polymer beads made according to the present invention typically have a molecular weight of about 100 kDalton, a glass transition temperature of about 80-120° C. and a particle size of about 50 to 500 µm such as e.g. 200 to 500 µm (X-50). Due to high Tg of the acrylic polymer beads no anti-caking agent is needed to prevent the beads from sticking during storage even at elevated temperature. Furthermore, the residual monomer content prior to drying is low enough to come below the limit required for personal care applications after an extended drying step at about 80-100° C. such as e.g. at 90° C., i.e. below 250 ppm and in particular even below 100 ppm.

The acrylic polymer beads according to the invention typically have an acid value of about 125-145 mg KOH/g.

The glass transition temperature $T_g$ is the limit at which, according to G. Kanig (Kolloid-Zeitschrift & Zeitschrift fur Polymere, Vol. 190, page 1, equation 1) the polymer changes from a glassy, brittle state to a rubbery state. Tg values of polymers may e.g. be determined experimentally using techniques such as differential scanning calorimetry DSC.

Acrylic polymer beads according to the present invention are e.g. available at DSM Nutritional products Ltd. under the Tradename TILAMAR® Fix A1000 (INCI: Acrylates Copolymer, Chemical Name: polymer with 2-methyl-2-propenoic acid, butyl 2-methyl-2-propenoate, ethyl 2-methyl-2-propenoate and ethyl 2-propenoate, CAS Number: 1070166-98-1).

After neutralization e.g. with 2-amino-2-methylpropanol (AMP), the acrylic polymer beads according to the invention are perfectly soluble in water, in ethanol and in mixtures of both making them suitable for a wide range of applications. In particular, the acrylic polymer beads according to the invention exhibit a good compatibility with cosmetic ingredients making them especially suitable for cosmetic applications such as in particular hair care applications.

Thus, the invention in a further embodiment relates to cosmetic compositions comprising acrylic polymer beads according to the invention and a cosmetically acceptable carrier. The term "cosmetic composition" as used herein refers in particular to cosmetic compositions that can be topically applied to mammalian keratinous tissue such as e.g. human skin or scalp. The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), $4^{th}$ edition, 1992.

The term cosmetically acceptable carrier refers to all carriers and/or excipients and/or diluents conventionally used in cosmetic compositions.

The amount of the acrylic polymer beads according to the present invention in the cosmetic compositions, in particular in the hair care preparations according to the invention may easily be chosen by a person skilled in the art in an amount suitable for the desired application. Preferably, a concentration of 0.01-20 wt.-%, most preferred of 0.05-10 wt.-% such as in particular about 5 wt.-% based on the total weight of the cosmetic composition is used.

Next to their good solubility in water, alcohol as well as mixtures thereof the acrylic polymer beads according to the invention also show excellent hair styling properties such as e.g. excellent high humidity curl retention. Thus, the acrylic polymer beads according to the invention are in particular suitable for hair styling applications.

Thus, in another embodiment the present invention relates to hair care preparations such as in particular hair styling preparations (e.g. aqueous hair styling preparations) comprising the acrylic polymer beads according to the invention.

The hair care preparations according to the present invention may be in the form of a (aerosol) spray, (aerosol) foam, gel, gel spray, cream, lotion, liquid or a wax. Hair sprays comprise as well aerosol sprays as pump sprays without propellant. Hair foams comprise as well aerosol foams as pump foams without propellant. Hair sprays and hair foams comprise mainly or exclusively water soluble or water dispersible components. If the components used in hair sprays or hair foams according to the invention are water dispersible, then they may be in the form of micro dispersions with particle sizes of usually 1-350 nm, preferably 1-250 nm. The solid content of such preparations is typically in the range of 0.5 to 20 wt. % of the total weight of the preparation. Such micro dispersions normally do not need further emulsifiers or tensides for their stabilization. In particular the hair styling preparations according to the invention are in the form of styling creams, styling gels, liquid hair-setting preparations, hair foams or hairsprays.

The acrylic polymer beads according to the present invention further exhibit an excellent solubility in ethanol or water as well as in mixtures thereof which is a prerequisite for the formulation of hair styling preparations such as hairsprays. Furthermore, the compatibility of ethanol solutions comprising the acrylic polymer beads according to the invention with commercial propellants (propane/butane, DME) is comparable to that of Luvimer® acrylate emulsion polymers and thus the beads are in particular suitable for use in aerosol hair sprays.

The hair care preparations such as in particular the hair styling preparations may also contain other hair fixative resins, neutralizers, surfactants, solvents, propellants, other preservatives, thickeners, UV-filters and other additives usually employed in such preparations.

The amount of the acrylic polymer beads according to the present invention in hair styling preparations is preferably selected within a concentration range of 0.01-20 wt.-%, more preferably within a concentration range of 0.1-10 wt.-% such as in particular within a concentration range of 1 to 10 wt.-% such as about 5 wt.-% based on the total weight of the hair styling preparation.

Other hair fixative resins may optionally be added to the hair care preparations to provide other properties which may be desired by the formulator, such as a "stiffer" hold of the hair. The other hair fixative resins may be soluble or insoluble in the hair styling preparation. The other hair fixative resins may be present in the hair styling preparation at a concentration of from 0.5 to 6.0 weight percent, preferably from 1.0 to 3.0 weight percent, based on the total weight of the hair styling preparation.

The other hair fixative resins which are suitable in the hair care preparation include for example butyl acrylate/ethyl acrylate/methacrylic acid copolymers; polyvinyl pyrrolidone, vinyl pyrrolidone/vinyl acetate copolymers; octylacrylamide/acrylates/butyl-aminoethylmethacrylate copolymers; vinylcaprolactam/vinylpyrrolidone/dimethylamino-ethylmethacrylate copolymers; methacryloyl ethyl-betaine/methacrylate copolymers; methacrylic acid/methacrylic ester copolymer; methacrylic acid/acrylic acid ester copolymers, alkylester of the copolymer of vinyl methyl ether and maleic anhydride; hydroxyethylcellulose quaternized with diallyl dimethyl ammonium chloride, quaternized vinyl pyrrolidone/dimethylaminoethylmethacrylate copolymer, or combinations thereof.

Neutralizers are preferably present in the hair care preparation when the hair fixative resins contain acidic groups, such as carboxylic acid groups, to promote solubility of the resin in the aqueous hair styling composition. For example, the acrylic hair fixative resin is preferably fully neutralized.

Bases which will neutralize the hair fixative resins include for example amines, alkali or alkaline earth metal hydroxides, ammonium hydroxide or combinations thereof. Suitable amine neutralizers include for example 2-amino-2-methyl propanediol, 2-amino 2-methyl propanol, N,N-dimethyl-2-amino-2-methyl-1-propanol, mono-isopropanolamine, tri-iso-propanolamine, ethanolamine, triethanolamine, morpholine or combinations thereof. Suitable alkali or alkaline earth metal hydroxides include for example sodium hydroxide potassium hydroxide, or combinations thereof. Preferably, the neutralizer is selected from the group consisting of 2-amino 2-methyl propanediol, 2-amino-2-methyl propanol, N,N dimethyl 2-amino 2-methyl propanol, potassium hydroxide, triethanolamine, triisopropanolamine, or combinations thereof.

The amount of neutralizer added to the hair care preparation is preferably that amount to provide solubility of the hair fixative resin in the hair styling composition. Preferably, in a hair styling preparation containing 35 weight percent or less VOC, from 40 to 100 mole percent of the acid groups on the hair fixative resin are neutralized. For a VOC hair styling composition containing greater than 35 weight percent VOC, preferably greater than 50 mole percent of the acid groups on the hair fixative resin are neutralized.

One or more surfactants may be added to the hair care preparation. When surfactants are present in the hair care preparation, they are preferably present at a concentration of from 0.001 to 1.0 wt.-%, based on the total weight of the composition. The surfactants which may be used in the hair care preparation include for example anionic, cationic, non-ionic, or amphoteric surfactants. For example, suitable surfactants include PPG 28 Buteth 35, PEG 75 lanolin, perfluoropolymethyl isopropyl ether, octoxynol-9, PEG-25 hydrogenated castor oil, polyethylene terephthalate, polyethylene glycol 25 glyceryl trioleate, oleth-3 phosphate, PPG-5-ceteth-10 phosphate, PEG-20 methyl glucose ether, glycereth-7-triacetate, glycereth-7-benzoate, fatty acid ester of polysorbate (TWEEN), or n-alkyl substituted lactam such as n-octyl pyrrolidone, or combinations thereof.

One or more siloxane derivatives may be present in the hair care formulation. When they are used, they are preferably present in a concentration from 0.001 to 1.0 wt.-%, based on the total weight of the composition. The siloxane derivatives include for example dimethicones, phenyl trimethicones, dimethiconols, amodimethicones, alkoxylated dimethicones e.g. PEG-12 dimethicone or methoxy PEG/PPG-7/3 aminopropyl dimethicone.

One or more solvents may be added to the hair care preparation of the present invention. The solvents may or may not be VOC. The amount of solvent added to the hair care preparation can be selected in the range of about 100 wt.-% or less, such as in particular in the range of 55 wt.-% or less based on the total weight of the hair care preparation. Suitable solvents include for example $C_1$ to $C_{12}$ straight or branched chain alcohols such as methanol, ethanol, isopropanol, or propanol or combinations thereof.

In a hair care preparation using an aerosol spray, one or more propellants are used. The propellants may or may not be VOC. Preferably, the propellants are used at a total concentration of from 10 to 70 wt.-%; and more preferably from 30 to 60 wt.-% based on the total weight of the hair care preparation. Propellants include for example n-butane, isobutane, dimethyl ether; dimethoxymethane, difluoroethane, chlorodifluoroethane, chlorodifluoromethane, other chlorofluorocarbons or combinations thereof. Preferred propellants are dimethyl ether, 1,1-difluoroethane, n-butane, isobutane or combinations thereof. These propellants are commercially available.

Other preservatives which may be used in the hair care preparation include for example isothiazolones, benzyl alcohol, or imidazolidinylurea. The other preservatives are preferably used in an amount of about 0.001 to 1.0 wt.-% based on the total weight of the hair care preparation.

One or more thickeners may be desirable in a hair care preparation which is applied to the hair in form of a mousse or styling gel. Suitable thickeners include for example polycarboxylic acid thickeners such as acrylates/steareth-20 methacrylate copolymer, carbomers, acrylates copolymer, or acrylates $C_{10-30}$ acrylate crosspolymer; polyethoxylated urethane thickeners, or polyamide thickeners. Other suitable thickeners are based on natural polymers such as polysaccharides or polyamides and can be chemically modified. Such thickeners include for instance hydroxyethyl celluloses, hydroxypropyl celluloses, xanthan gum, gelatine, agar-agar, carragenens, alginates or mixtures thereof. The thickeners are preferably used in an amount of about 0.001 to 5.0 wt.-% based on the total weight of the hair care preparation.

One or more light screening agents may be desirable in a hair care preparation according to the invention. The light screening agents are advantageously selected from UV-A, UV-B, UV-C and/or broadband filters such as in particular from the commercially available and widely used UV-filter substances octocrylene (PARSOL® 340), 4-methyl benzylidene camphor (PARSOL® 5000), ethylhexyl methoxycinnamate (PARSOL® MCX), ethylhexyl triazone (Uvinul® T-150), diethylhexyl butamido triazone (Uvasorb® HEB), 2,2'-methylene-bis-(6-(2H-benzotriazole-2-yl)-4-(1,1,3,3,-tetramethylbutyl)-phenol (Tinosorb® M), bis-ethylhexyloxyphenol methoxyphenyl triazine (Tinosorb® S), 2,2-(1,4-phenylene)bis-(1H-benzimidazol-4,6-disulfonic acid (NeoHeliopan® AP), 2-(4-Diethylamino-2-hydroxy-benzoyl)-benzoic acid hexylester (Uvinul® A plus), polysilicone-15 (PARSOL® SLX), 2-phenyl benzimidazole sulfonic acid (PARSOL® HS), ethylhexyl salicylate (PARSOL® EHS), homomethyl salicylate (PARSOL® HMS), Benzophenone-3 (Uvinul® M 40), Benzophenone-4 (Uvinul® MS 40), PEG-25 PABA, as well as mixtures thereof.

The light screening agents are generally present in the compositions according to the invention in proportions ranging from 0.001 to 5 wt.-%, preferably ranging from 0.01 to 1 wt.-%, most preferably ranging from 0.02 to 0.5 wt.-% with respect to the total weight of the composition.

Additionally other additives, such as those commonly used by those skilled in the art may be added to the hair care preparation according to the invention. The other additives used in the hair care preparations will depend upon the type of hair care preparation desired. Other additives include for example fragrances; moisturizers such as sorbitol, propane diol, butylene glycol, glycerin, hydrolyzed silk protein, or hydrolyzed wheat protein; detangling aids such as panthenol; conditioning agents such as those disclosed in U.S. Pat. No. 5,164,177 emulsifiers; antistatic aids, extracts, proteins, vitamins, dyes, tints, colorants or combinations thereof. The other additives are typically present from 0.005 to 5 wt.-%; more preferably from 0.01 to 1 wt.-% based on total weight of the hair care preparation.

Additional other additives, as well as additional surfactants, solvents, other preservatives, and thickeners, which may be suitable in the hair care compositions may be found in the International Cosmetic Ingredients Dictionary, 5th Edition, 1993, published by the CTFA in Washington D.C.

The following examples are provided to further illustrate the processes and compositions of the present invention. These examples are illustrative only and are not intended to limit the scope of the invention in any way.

EXAMPLE 1

The polymerization reactions were conducted in a glass 3-necked reaction flask using stainless steel baffle and stirrer equipped with nitrogen inlet.

Hydroxylethylcellulose stabilizer (2.4 g) was weighed into the reaction flask containing distilled water (1,105 g). 480 g of a monomer mixture consisting of n-butylmethacrylate (BMA), ethylmethacrylate (EMA), ethylacrylate (EA) and methacrylic acid (MMA) in the ratios as indicated below was weighed into a separate stirred feedtank containing di-lauroylperoxide (3.6 g) as chain starter and dodecylmercaptane chain transfer agent (1.9 g). After homogenizing the feedtank, the mixture was transferred to the reaction flask and under constant nitrogen purge slowly heated to 75° C. This temperature was maintained for 4 hrs to reach hard bead stage. After establishing hard bead stage, reaction flask content was subsequently heated to 85° C. and left at this temperature for another 2 hrs. Accordingly the reactor contents were cooled, the final suspension polymer filtered, washed and allowed to dry at 40-50° C. for 14-16 hrs yielding the respective polymer beads in 90-95% yield. When indicated, the obtained acrylic polymer beads were furthermore subjected to an extended drying process at 90° C. for another 14-16 hrs resulting in residual monomer contents of less than 210 ppm or even less than 100 ppm.

The residual monomer content was analysed via Headspace Gas Chromatographie, the molecular weight (MW) was determined by Gel Premeation Chromatographie, the Tg by Differential Scanning Calometrie (DSC) and the particle size (PS) determination is done via a so-called Malvern Hydro 2000 Mastersizer. This instrument optically (by laser diffraction) determines a volume distribution of the sample submitted in a water environment. The X50 mentioned is the average particle size of the total volume distribution as determined.

TABLE 1

Results of the reduction of the residual monomer content by EMA

| | acrylic polymer building blocks | | | | total monomer content |
|---|---|---|---|---|---|
| No. | BMA [wt %] | EMA [wt %] | EA [wt %] | MAA [wt %] | after drying at 40° C. [ppm] |
| 1 | 75 | — | 5 | 20 | 510 |
| 2 | 70 | — | 10 | 20 | 630 |
| 4 | 60 | — | 20 | 20 | 545 |
| 5 | 60.00 | 10.65 | 9.80 | 19.55 | 210 |

TABLE 2

Influence of the ratios and concentration levels on the residual monomer content

| No. | BMA [wt %] | EMA [wt %] | EA [wt %] | MAA [wt %] | EMA/EA ratio (w/w) | total monomer content after drying in [ppm] at 40° C. | at 90° C. | $T_g$ ° C. | PS X-50 µm | MW Dalton |
|---|---|---|---|---|---|---|---|---|---|---|
| 1 | 60.70 | 10.00 | 9.75 | 19.55 | 1.03 | 260 | 125 | 99 | 396 | 107.5 |
| 2 | 60.00 | 10.65 | 9.80 | 19.55 | 1.09 | 210 | 115 | 98 | 387 | 105.2 |
| 3 | 44.20 | 20.40 | 15.00 | 20.40 | 1.36 | 140 | 60 | 95 | 251 | 98.4 |
| 4 | 44.10 | 20.60 | 10.30 | 25.00 | 2.00 | 410 | 190 | 118 | 323 | 107.9 |
| 5 | 50.00 | 20.00 | 10.00 | 20.00 | 2.00 | 205 | 70 | 101 | 258 | 100.5 |
| 6 | 55.85 | 19.45 | 9.70 | 15.00 | 2.01 | 190 | 60 | 84 | 285 | 94.8 |
| 7 | 40.00 | 29.35 | 10.20 | 20.45 | 2.88 | 230 | 120 | 105 | 273 | 93.5 |
| 8 | 39.30 | 30.00 | 10.25 | 20.45 | 2.93 | 225 | 115 | 105 | 290 | 99.1 |
| 9 | 55.80 | 19.60 | 5.00 | 19.60 | 3.92 | 310 | 205 | 107 | 282 | 102.2 |

As can be retrieved from table 2 optimal results are obtained when the ratio of EMA to EA (w/w) is selected in the range of 1.3 to 2 and MAA is used in an amount of 15-22%.

Comparative Trial

The experiment outlined above is repeated replacing EMA with either methyl methacrylate (MMA) or Itaconic acid (ITA) as indicated below. As can be retrieved from table 2a, the replacement, however, resulted either in no product at all as the reaction failed completely due to agglomeration of the monomers (entry 2), respectively yielded in a significantly lower yield (71%) and a significantly higher residual monomer content (7058 ppm) as the ITA is not incorporated into the polymer (entry 3).

TABLE 2a

| | acrylic polymer building blocks | | | | | | total monomer content |
|---|---|---|---|---|---|---|---|
| No. | BMA [wt %] | EMA [wt %] | EA [wt %] | MAA [wt %] | MMA [wt %] | ITA [wt %] | yield | after drying at 40° C. [ppm] |
| 1 | 50 | 20 | 10 | 20 | | | 95% | 205 |
| 2 | 50 | — | 10 | 20 | 20 | | 0% | — |
| 3 | 50 | — | 10 | 20 | | 20 | 71% | 7058 |

The results show that the monomer content of acrylic polymer beads according to the invention can be significantly reduced by copolymerization of EMA. Furthermore, the acrylic polymer beads according to the present invention can be obtained in good yields and high purity when compared to the use of other monomer building blocks instead of EMA. Additionally, the acrylic polymer beads according to the invention also exhibit a very low total monomer content when compared to the market benchmark for hair styling applications such as e.g. Luvimer® 100P (acrylate emulsion polymer consisting of methacrylic acid, tert-butyl acrylate and ethyl acrylate) which exhibits a total monomer content of 425 ppm when measured according to the method described above.

EXAMPLE 2

Solubility of Acrylic Polymer Beads in Ethanol, in Water and in Mixtures Thereof Mixtures of Ethanol/Water were tested according to the US-VOC-guidelines as "VOC 80" and "VOC 55" formulation using the beads of table 2. The acrylic polymer beads can be easily incorporated either into the ethanol or into the water phase of the VOC formulation:

Solubility in Ethanol 5 wt.-% of the acrylic polymer beads according to table 2 were easily dispersed in 20 wt.-% of the amount of ethanol needed in the respective VOC formulation. Afterwards AMP (in an amount sufficient to achieve a neutralization level of 90-100%) is added and the dispersions are stirred for 10-15 min to dissolve the respective beads. The residual amounts of ethanol as well as water (for VOC 80 and 55) are added to complete the formulation to 100%.

Solubility in Water

30% of the calculated amount of water needed in the respective VOC formulation is heated up to 60° C. Then 5 wt.-% of the acrylic polymer beads according to table 2 are dispersed, AMP (in an amount sufficient to achieve a neutralization level of 90-100%) is added and the dispersions are stirred at 60° C. until all beads are dissolved (10-15 min). Then, the rest of the water and/or the ethanol are added.

All VOC 80 as well as the VOC 55 formulations comprising the respective beads according to table 2 were clear and did not contain any precipitate (visual judgement).

EXAMPLE 3

Assessment of the Solubility

The solubility of 5 wt.-% acrylic polymer beads in standard hair care preparations was determined by preparation of the formulations as indicated in table 3 according to standard procedures and determination of the turbidity with a HACH 2100 N IS Turbidimeter, 115 Vac according ISO 7027 (The threshold for turbidity is at NTU≥5. (NTU<5 means visibly clear solution)). Furthermore, the solutions were assessed visually.

TABLE 3

Solubility

| Solution | Composition | Beads according to entry 3 table 2 visual | NTU* | TILAMAR Fix A1000 visual | NTU* |
|---|---|---|---|---|---|
| High VOC | acrylic polymer beads: 5 wt.-% AMP-95: 0.96%, Ethanol Ad. 100 | clear | <2.6 | clear | <2.6 |
| VOC 80 | acrylic polymer beads: 5 wt.-% AMP-95: 0.96 wt.-% Ethanol: 80 wt.-% Water Ad. 100 | clear | <0.8 | clear | <0.8 |
| VOC 55 | acrylic polymer beads: 5 wt.-% AMP-95: 0.96 wt.-% Ethanol: 55 wt.-% Water Ad. 100 | clear | <0.7 | clear | <0.7 |
| No VOC | acrylic polymer beads: 5 wt.-% AMP-95: 0.96 wt.-% Water Ad. 100 | clear | <2.2 | clear | <2.2 |

As to be seen, all values are considerably below the threshold for "crystal clear" NTU=5 and the formulation are clear.

EXAMPLE 4

High Humidity Curl Retention Test

Hair Tresses (Kerling; Art. Nr. 826 500) are cut in switches of 2 cm width. Each switch is washed twice with 0.5 mL of a Cleansing Shampoo (10% Sodium Laureth Sulfate/4% Sodium Chloride): 30 s foaming, 90 s rinsing with warm water. The switches are combed 5 times and dried in a climate room at 20° C. and 65% relative humidity for at least 4 hours. The weight of the switches is standardized under these conditions for 2 g+/−0.2 g for hair (without rubber coating). Afterwards the switch is dampened with 1 g water, and evenly wetted with 0.3 g of polymer solution (5 wt.-% of TILAMAR® Fix A1000 in EtOH, 100% neutralized with AMP-95): application with syringe from root to tip and comb 5 times. Then, the switch is curled with a spiral curler of 12 mm diameter (Basler Haarkosmetik Art. 12939).

The curler with the hair is dried for 40 min at 45° C. Then, the curler is left in the climate room at 20° C./65% rel. humidity over night. The curl is removed carefully from the curler, lay at the table and the starting length $L_o$ is taken. Than, the curl is hung up at the rubber coating in the climate chamber at 20° C./90% rel. humidity, and the Length $L_t$ is taken after following times: 0 min, 15 min, 30 min, 45 min, 60 min, 90 min, 120 min, 240 min and 360 min. For each sample, three hair switches are prepared. The curl retention values are calculated as follow:

$$C.R. \ [\%] = \frac{L - L_t}{L - L_0} \times 100$$

L=Length of uncurled Hair (230 mm)
Lo=Length of the curl after drying at the table
Lt=Length of hanging curl in after time t The Curl Retention of one sample is obtained as the mean of the three calculated curl retention values of the three switches.

Every Curl Retention is measured together with a benchmark chosen from a market polymer.

The results are summarized in table 4:

TABLE 4

Curl Retention in % at 20° C./90% r.H. (5 wt.-% solids in EtOH, 100% Neutralizationl)

| Product | Time [min] | | | | | | | | |
|---|---|---|---|---|---|---|---|---|---|
| | 0 | 15 | 30 | 45 | 60 | 90 | 120 | 240 | 360 |
| Polymer Beads according to the invention (TILAMAR ® Fix A 1000) | 96.8 | 90.3 | 80.6 | 72.0 | 69.9 | 62.4 | 59.1 | 53.8 | 52.7 |
| Market Benchmark | 95.7 | 88.2 | 77.4 | 69.9 | 62.4 | 55.9 | 49.5 | 44.1 | 40.9 |

It is clear to be seen, that the acrylic polymer beads according to the invention, especially on long term, perform better than the market benchmark, i.e. an acrylate emulsion polymer consisting of MAA, tert-butyl acrylate and EA (Luvimer® P100).

EXAMPLE 5

Salon Test

Bulk solutions comprising the ingredients listed in table 5 was prepared and the bulk solutions was bottled as aerosol hair spray as outlined in table 6 according to standard procedures.

TABLE 5

Preparation of hair sprays 'A' and 'B'

| Ingredient Name | INCI | A % w/w | B % w/w |
|---|---|---|---|
| Ethanol | Alcohol | 92.10 | 92.10 |
| TILAMAR ® Fix A1000 | Acrylates Copolymer | 6.00 | — |
| Luvimer P100 | | — | 6.00 |
| AMP-Ultra PC 2000 | Aminomethyl Propanol | 1.27 | 1.27 |
| D-Panthenol 75 L | Panthenol | 0.18 | 0.18 |
| Neo Heliopan, Type E 1000 | Isoamyl p-Methoxycinnamate | 0.09 | 0.09 |
| Pö Color Express 351 580 | Parfum | 0.18 | 0.18 |
| Dow Corning 193 Surfactant | PEG-12 Dimethicone | 0.18 | 0.18 |

TABLE 6

| Ingredient Name | % w/w |
| --- | --- |
| Bulk Solutions according to table 5 | 70.00 |
| Propane/Butane 2.5bar | 20.00 |
| isoButan | 10.00 |

General Test Design

All tests are carried out in a regular hairdresser studio with common equipment on 10 panellists. The models are treated according to common procedures of hair washing, cutting, colouring, bleaching, perming, drying (air or blow-dry) etc. Each model is styled according to his/her wishes. The Hairspray is finally sprayed from a distance of 20-30 cm around the hair (not directly into eyes and face) at an application rate (mid-long hair, ~15 cm) of 5 s per half-side (increased for longer hair).

After finishing the application, the stylist starts with the evaluation of the product performance using his fingers, his hands, a comb, a brush and his eyes.

Result

Hair spray 'A' was assessed in a half side test against benchmark hair spray 'B'. As can be retrieved from table 6, hairspray 'A' comprising the inventive beads was overall rated significantly better in regard to its performance in view of hold, crosslinking, shine and creation of style.

TABLE 6

|  | 1 | 2 | 3 | 4 | 5 | 6 | 7 | 8 | 9 | 10 | Mean |
| --- | --- | --- | --- | --- | --- | --- | --- | --- | --- | --- | --- |
| Creation of style | 3 | 3 | 3 | 3 | 2.5 | 3 | 3 | 2.5 | 3 | 3 | 2.90 |
| Hold | 2.5 | 3 | 2.5 | 2 | 2 | 3 | 3 | 3 | 3 | 3 | 2.70 |
| Shine | 0 | 0 | 0 | 1 | 1 | 0 | 0 | 0 | −1 | 1 | 0.20 |
| crosslinking | 2.5 | 2 | 2.5 | 3 | 3 | 2.5 | 3 | 3 | 3 | 3 | 2.75 |

−1 = slightly worse than benchmark
0 = no difference to benchmark
1 = slightly better than benchmark
2 = better than benchmark
3 = significantly better compared to benchmark

EXAMPLE 6

Propellant Compatibility

Add 20 mL of 5% TILAMAR® Fix A1000 Polymer Solution in Ethanol into the test tube. Close the glass. Fill in propellant via the aerosol valve (can-to-can).
Propellants: Propane/Butane 2.5 bar, respectively DME
Test criteria: One or two phases
 Clear, no clouds, no precipitation
Results: Cloud point at 47% propane/butane (at 5% solids).
 Clear until 32% DME (at 5% solids). No precipitation observed These results show that the acrylic polymer beads according to the invention exhibit a broad propellant compatibility.

EXAMPLE 7

Formulations

The acrylic beads according to the invention such as in particular TILAMAR® Fix A1000 (INCI: Acrylates Copolymer, Chemical Name: polymer with 2-Methyl-2-propenoic acid, butyl 2-methyl-2-propenoate, ethyl 2-methyl-2-propenoate and ethyl 2-propenoate, CAS Number: 1070166-98-1) exhibits a unique product form, superior high humidity curl retention, excellent propellant compatibility, easy handling and a natural feel on hair. Thus, the acrylic beads according to the invention as in particular TILAMAR® Fix A1000 can be incorporated into a great variety of product forms as illustrated below without being limited thereto:

7.1. VOC Pump Sprays

| No | Ingredients | INCI Name | VOC 80 wt.-% | VOC 55 wt.-% |
| --- | --- | --- | --- | --- |
| 1 | Ethanol | Alcohol | 80 | 55.00 |
| 2 | Water demin. | Aqua | Ad 100 | Ad 100 |
| 3 | Polymer Beads according to the invention, in particular TILAMAR® Fix A1000 | Acrylates Copolymer | 5.00 | 5.00 |
| 4 | AMP-95 | Aminomethyl Propanol | 1.06 | 1.38 |
| 5 | PARSOL® 340 | Octocrylene | 0.10 | — |
| 6 | PARSOL® MCX | Ethylmethoxycinnamate | — | 0.15 |
| 7 | D-PANTHENOL 75 L | Panthenol | 0.10 | 0.10 |
| 8 | PEG-12 Dimethicone | PEG-12 Dimethicone | 0.15 | — |
| 9 | Phenyl Trimethicone | Phenyl Trimethicone | — | 0.15 |
| 10 | Fragrance | Fragrance | 0.20 | 0.20 |

Procedure: Mix Pos. 1 to Pos. 10.

7.2. Solid Styling Wax

| No | Name | INCI Name | wt.-% |
| --- | --- | --- | --- |
| 1 | Water demin. | Aqua | Ad 100 |
| 2 | Isoceteth-20 | Isoceteth-20 | 22.00 |
| 3 | PEG-7 Glyceryl Cocoate | PEG-7 Glyceryl Cocoate | 10.00 |
| 4 | Polymer Beads according to the invention, in particular TILAMAR® Fix A1000 | Acrylates Copolymer | 6.00 |
| 5 | Hydrogenated Polydecene | Hydrogenated Polydecene | 6.00 |
| 6 | Glycerin | Glycerin | 4.00 |
| 7 | Quaternium-26 (58%) in Propylene Glycol | Quaternium-26 (58%) in Propylene Glycol | 2.00 |
| 8 | AMP-95 | Aminomethyl Propanol | 1.27 |
| 9 | Propylparabene | Propylparabene | 0.20 |
| 10 | Fragrance | Fragrance | 1.00 |

Procedure: Mix Pos. 1 and Pos. 8, and heat them up to at 60° C. Add Pos. 4 and stir until a clear solution has been formed. Dissolve Pos. 9 in Pos. 6 under heating. Add Pos. 2, 3, 5, 7 and the Glycerin solution of Pos. 9 to the polymer solution and heat the solution up to 80° C. After 10 min, cool down to 40° C., add the fragrance with stirring and fill the mass into a jar. After several hours, the solid wax is formed.

7.3. Fibre Styling Pomade

| No | Name | INCI Name | wt.-% |
| --- | --- | --- | --- |
| 1 | Water | Aqua | Ad 100 |
| 2 | Polymer Beads according to the invention, in particular TILAMAR® Fix A1000 | Acrylates Copolymer | 4.00 |
| 3 | AMP-95 | Aminomethyl Propanol | 1.27 |
| 4 | Sorbitol 70% | Sorbitol 70% | 4.00 |
| 5 | PEG-90M | PEG-90M | 0.50 |
| 6 | Methylparabene | Methylparabene | 0.25 |

-continued

| No | Name | INCI Name | wt.-% |
|---|---|---|---|
| 7 | PEG 150/Stearyl Alcohol/ SMDI Copolymer (19% in water) | PEG 150/Stearyl Alcohol/ SMDI Copolymer (19% in water) | 2.20 |
| 8 | Lanolin | Lanolin | 3.00 |
| 9 | Cetyl Dimethicone | Cetyl Dimethicone | 3.00 |
| 10 | Dicaprylyl Carbonate | Dicaprylyl Carbonate | 7.00 |
| 11 | Propylparabene | Propylparabene | 0.20 |
| 12 | Fragrance | Fragrance | 1.00 |
| 13 | Glycol Distearate | Glycol Distearate | 3.00 |
| 14 | Cyclopentasiloxene & Dimethicone Crosspolymer | Cyclopentasiloxene & Dimethicone Crosspolymer | 2.40 |

7.4. Styling Cream

| No | Name | INCI Name | wt.-% |
|---|---|---|---|
| 2 | Water | Aqua | Ad 100 |
| 3 | Polymer Beads according to the invention, in particular TILAMAR ® Fix A1000 | Acrylates Copolymer | 5.50 |
| 4 | PEG 150/Stearyl Alcohol/ SMDI Copolymer (19% in water) | PEG 150/Stearyl Alcohol/ SMDI Copolymer (19% in water) | 2.20 |
| 5 | Acrylic Acid/ VP-Crosspolymer | Acrylic Acid/ VP-Crosspolymer | 1.20 |
| 6 | AMP Ultra PC 2000 | Aminomethyl Propanol | 1.07 |
| 7 | Fragrance | Fragrance | 0.35 |
| 8 | Styrene/Acrylates Copolymer (40% in water) | Styrene/Acrylates Copolymer (40% in water) | 0.20 |
| 9 | Silicone Quaternium-16 & Undeceth-11 & Butyloctanol & Undeceth-5 | Silicone Quaternium-16 & Undeceth-11 & Butyloctanol & Undeceth-5 | 1.20 |
| 10 | Ethyl Panthenol | Panthenyl Ethyl Ether | 0.25 |
| 11 | Methylisothiazolinone (10% in Propylene Glycol) | Methylisothiazolinone (10% in Propylene Glycol) | 0.10 |
| 12 | AMP Ultra PC 2000 to adjust pH | Aminomethyl Propanol | 0.20 |
| 13 | PEG-90M | PEG-90M | 0.10 |

7.5. Fine Modelling Sprizz

| No | Name | INCI Name | wt.-% |
|---|---|---|---|
| 1 | Ethanol | Alcohol denat. | 25.00 |
| 2 | Water demin. | Aqua | Ad 100 |
| 3 | Polymer Beads according to the invention, in particular TILAMAR ® Fix A1000 | Acrylates Copolymer | 3.75 |
| 4 | Acrylic Acid/ VP-Crosspolymer | Acrylic Acid/ VP-Crosspolymer | 0.95 |
| 5 | Silicone Quaternium-16 & Undeceth-11 & Butyloctanol & Undeceth-5 | Silicone Quaternium-16 & Undeceth-11 & Butyloctanol & Undeceth-5 | 2.20 |
| 6 | AMP-95 | Aminomethyl Propanol | 0.74 |
| 7 | Fragrance | Fragrance | 0.20 |
| 8 | PARSOL SLX | Polysilicone-15 | 0.25 |
| 9 | AMP-95 to adjust pH | Aminomethyl Propanol | q.s. |
| 10 | Ethyl Panthenol | Panthenyl Ethyl Ether | 0.20 |
| 11 | Silica & Titanium Dioxide (EU: CI 77891) & Tin Oxide (EU: CI 77861) | Silica & Titanium Dioxide (EU: CI 77891) & Tin Oxide (EU: CI 77861) | 0.10 |

Procedure: Adjust pH with Pos. 9 to 7.7.->Viscosity=2000 mPas; add water to 100%

7.6. Aerosol Hairspray "Strong Hold"

| No | Name | INCI Name | wt.-% |
|---|---|---|---|
| 1 | Ethanol | Alcohol denat. | Ad 100 |
| 2 | AMP-95 | Aminomethyl Propanol | 1.27 |
| 3 | Polymer Beads according to the invention, in particular TILAMAR ® Fix A1000 | Acrylates Copolymer | 6.00 |
| 4 | D-PANTHENOL 75 L | Panthenol | 0.18 |
| 5 | Neo Heliopan E 1000 | Isoamyl p-Methoxycinnamate (Amiloxate; USAN) | 0.09 |
| 6 | Fragrance | Fragrance | 0.18 |
| 7 | PEG-12 Dimethicone | PEG-12 Dimethicone | 0.18 |

Procedure: This solution is bottled in an appropriate can (aluminium, tinplate), crimped with an aerosol valve and a propellant is added. The propellant, the ratio of effective solution:propellant and the actuator are chosen according to the product requirements as spray rate, spray pattern, particle size and particle size distribution. A typical composition would be: 60% Effective Solution; 40% propane/butane 2.5 bar (high VOC) or 55% Effective solution & 45% HF 152A for a water-freeVOC.55 Hairspray.

7.7. Pump Shine & Hold Hair Spray with Natural Feel

| Phase | Ingredients | INCI Name | wt.-% |
|---|---|---|---|
| A | Ethanol | Alcohol denat. | 25.00 |
|  | AMP Ultra PC 2000 | Aminomethyl Propanol | 0.98 |
|  | Polymer Beads according to the invention, in particular TILAMAR ® Fix A1000 | Acrylates Copolymer | 4.60 |
| B | Ethanol | Alcohol denat. | Ad 100 |
|  | PARSOL ® MCX | Ethylhexyl Methoxycinnamate (Octinoxate; USAN) | 0.10 |
|  | Ethyl Panthenol | Panthenyl Ethyl Ether | 0.18 |
|  | Pö Headstrong 167170 | Perfume | 0.23 |
|  | ARGAN OIL | *Argania Spinosa* Kernel Oil | 0.10 |
|  | Citrofol ®AL | Triethyl Citrate | 0.10 |
| C | Water dem. | Aqua | 11.00 |

Procedure: Part A, with stirring: Blend ethanol with AMP PC 2000. Add TILAMAR® Fix A1000 and stir until uniform. This part must be clear. Part B, with stirring: Add ethanol part II into the solution. Add step by step all other ingredients and stir until. Part C, with stirring: Add water into the solution. The solution must be clear.

7.8. Chic Shine Hairspray Luxurious Gloss and Addictive Shine

| Phase | Ingredients | INCI Name | wt.-% |
|---|---|---|---|
| A | Ethanol | Alcohol | 15.00 |
|  | AMP Ultra PC 2000 | Aminomethyl Propanol | 0.71 |
|  | Polymer Beads according to the invention, in particular TILAMAR ® Fix A1000 | Acrylates Copolymer | 3.36 |
| B | Ethanol | Alcohol | Ad 100 |
|  | Ethyl Panthenol | Panthenyl Ethyl Ether | 0.10 |
|  | PARSOL ® MCX | Ethylhexyl Methoxycinnamate (Octinoxate; USAN) | 0.10 |

-continued

| Phase | Ingredients | INCI Name | wt.-% |
|---|---|---|---|
|  | Pö Headstrong 167170 | Parfume | 0.14 |
|  | ARGAN OIL | *Argania Spinosa* Kernel Oil | 0.10 |
|  | Citrofol ® AL | Triethyl Citrate | 0.06 |
|  | Water dem. | Aqua | 1.20 |
| C | Propane/Butane 2.5 | Propane/Butane 2.5 | 40.00 |

Procedure: Part A, with stirring: Blend ethanol with AMP PC 2000. Add TILAMAR® Fix A 1000 and stir until uniform. This part must be clear.

Part B, with stirring: Add ethanol part II into the solution. Add step by step all other ingredients and stir until. Part C, Add propane/butane 7.9. Ringing Gel glossy Pomade with Vitamin E

| Phase | Ingredients | INCI Name | wt.-% |
|---|---|---|---|
| A | Water dem./part I | Water (Aqua) | 35.00 |
|  | Polymer Beads according to the invention, in particular TILAMAR ® Fix A1000 | Acrylates Copolymer | 4.50 |
|  | AMP Ultra PC 2000 | Aminomethyl Propanol | 0.97 |
| B | Cetiol HE | PEG-7 Glyceryl Cocoate | 17.00 |
|  | Eumulgin B3 | Ceteareth-30 | 22.00 |
|  | Tegosoft M | Isopropyl Myristate | 4.00 |
| C | Water dem./part II | Water (Aqua) | Ad 100 |
|  | Glycerin | Glycerin | 4.00 |
|  | FD & C Blue 1 | Blue 1 (CI 42090) | q.s. |
|  | Ronastar Noble Sparks | Calcium Aluminium Borsilikat & Silica & Titanium Dioxide (CI 77891) & Tin Oxide (CI 77861) | 0.001 |
| D | PÖ Headstrong 167170 | Parfume | 1.00 |
|  | Neolone 950 Preservative | Methylisothiazolinone | 0.10 |
|  | VITAMIN E ACETATE | Tocopheryl Acetate | 0.25 |

Procedure: Part A, with stirring: Blend water part I with AMP PC 2000. Add TILAMAR® Fix A1000 and stir until uniform. Heat to 80° C. This part must be clear. Part B, with stirring: In a separate vessel combine the Cetiol HE, Eumulgin B3 and Tegosoft M. Heat to the same temperature. With adequate mixing add step 2 to step 1 and maintain at 80° C. for 3-5 minutes. Adding step by step ingredients part C. Reduce mixing speed and cool to room temperature. Add the perfume, preservative and vitamin E at 50° C.-55° C. and continue cooling.

7.10. Elastic Flexible Hold Hairspray with UV Protection and Pro-Vitamin B5

| Phase | Ingredients | INCI Name | wt.-% |
|---|---|---|---|
| A | Ethanol | Alcohol | 25.00 |
|  | AMP Ultra PC 2000 | Aminomethyl Propanol | 1.27 |
|  | Polymer Beads according to the invention, in particular TILAMAR ® Fix A1000 | Acrylates Copolymer | 6.00 |
| B | Ethanol | Alcohol | Ad 100 |
|  | D-PANTHENOL 75 L | Panthenol | 0.18 |
|  | Neo Heliopan, Type E 1000 | Isoamyl p-Methoxycinnamate (Amiloxate; USAN) | 0.09 |
|  | Pö Color Express 351580 | Parfum | 0.18 |
|  | Dow Corning 193 | PEG-12 Dimethicone | 0.18 |

Procedure: Part A, with stirring: Blend ethanol with AMP PC 2000. Add TILAMAR® Fix A1000 and stir until uniform. This part must be clear. Part B, with stirring: Add ethanol part II into the solution. Add step by step all other ingredients and stir until.

7.11. Chic Shine Hairspray Luxurious Gloss and Addictive Shine

| Phase | Ingredients | INCI Name | wt.-% |
|---|---|---|---|
| A | Ethanol | Alcohol | 25.00 |
|  | AMP Ultra PC 2000 | Aminomethyl Propanol | 1.19 |
|  | Polymer Beads according to the invention, in particular TILAMAR ® Fix A1000 | Acrylates Copolymer | 5.60 |
| B | Ethanol | Alcohol | 65.37 |
|  | Ethyl Panthenol | Panthenyl Ethyl Ether | 0.17 |
|  | PARSOL ® MCX | Ethylhexyl Methoxycinnamate (Octinoxate; USAN) | 0.17 |
|  | Pö Headstrong 167170 | Parfume | 0.23 |
|  | ARGAN OIL | *Argania Spinosa* Kernel Oil | 0.17 |
|  | Citrofol ® AL | Triethyl Citrate | 0.10 |
|  | Water dem. | Aqua | 2.00 |

Procedure: Part A, with stirring: Blend ethanol with AMP PC 2000. Add TILAMAR® Fix A1000 and stir until uniform. This part must be clear. Part B, with stirring: Add ethanol part II into the solution. Add step by step all other ingredients and stir until.

7.12. Elastic Flexible Hold Hairspray with UV Protection and Pro-Vitamin B5

| Phase | Ingredients | INCI Name | wt.-% |
|---|---|---|---|
| A | Ethanol | Alcohol | 17.50 |
|  | AMP Ultra PC 2000 | Aminomethyl Propanol | 0.89 |
|  | Polymer Beads according to the invention, in particular TILAMAR ® Fix A1000 | Acrylates Copolymer | 4.20 |
| B | Ethanol | Alcohol | Ad. 100 |
|  | D-PANTHENOL 75 L | Panthenol | 0.13 |
|  | Neo Heliopan, Type E 1000 | Isoamyl p-Methoxycinnamate (Amiloxate; USAN) | 0.06 |
|  | Pö Color Express 351580 | Parfum | 0.13 |
|  | Dow Corning 193 | PEG-12 Dimethicone | 0.13 |
| C | Propane/Butane 2.5 | Propane/Butane 2.5 | 30.00 |

Procedure: Part A, with stirring: Blend ethanol with AMP PC 2000. Add TILAMAR® Fix A1000 and stir until uniform. This part must be clear. Part B, with stirring: Add ethanol part II into the solution. Add step by step all other ingredients and stir until. Part C. Add propane/butane.

7.13. Chic Shine Hairspray Luxurious Gloss and Addictive Shine

| Phase | Ingredients | INCI Name | wt.-% |
|---|---|---|---|
| A | Ethanol | Alcohol denat. | 17.50 |
|  | AMP Ultra PC 2000 | Aminomethyl Propanol | 0.83 |
|  | Polymer Beads according to the invention, in particular TILAMAR ® Fix A1000 | Acrylates Copolymer | 3.92 |

-continued

| Phase | Ingredients | INCI Name | wt.-% |
|---|---|---|---|
| B | Ethanol | Alcohol | Ad 100 |
|  | Ethyl Panthenol | Panthenyl Ethyl Ether | 0.12 |
|  | PARSOL ® MCX | Ethylhexyl Methoxycinnamate (Octinoxate; USAN) | 0.12 |
|  | Pö Headstrong 167170 | Parfume | 0.16 |
|  | ARGAN OIL | *Argania Spinosa* Kernel Oil | 0.12 |
|  | Citrofol ®AL | Triethyl Citrate | 0.07 |
|  | Water dem. | Aqua | 1.40 |
| C | Propane/Butane 2.5 | Propane/Butane 2.5 | 30.00 |

Procedure: Part A, with stirring: Blend ethanol with AMP PC 2000. Add TILAMAR® Fix A1000 and stir until uniform. This part must be clear. Part B, with stirring: Add ethanol part II into the solution. Add step by step all other ingredients and stir until. Part C: after bottling and crimping, add propane/butane.

7.14. Elastic Flexible Hold Hairspray VOC 55

| Phase | Ingredients | INCI Name | wt.-% |
|---|---|---|---|
| A | Ethanol | Alcohol | 17.50 |
|  | AMP Ultra PC 2000 | Aminomethyl Propanol | 0.89 |
|  | Polymer Beads according to the invention, in particular TILAMAR ® Fix A1000 | Acrylates Copolymer | 4.20 |
| B | Water | Aqua | Ad 100 |
|  | D-PANTHENOL 75 L | Panthenol | 0.13 |
|  | PARSOL ® MCX | Ethylhexyl Methoxycinnamate (Octinoxate; USAN) | 0.06 |
|  | Pö Color Express 351580 | Parfum | 0.13 |
|  | Dow Corning 193 | PEG-12 Dimethicone | 0.13 |
| C | Dimethylether (DME) | Dimethylether | 35.00 |

Procedure: Part A, with stirring: Blend ethanol with AMP PC 2000. Add TILAMAR® Fix A1000 and stir until uniform. This part must be clear. Part B, with stirring: Add water part II into the solution. Add step by step all other ingredients and stir until. Part C: After bottling and crimping, add DME.

EXAMPLE 8

The polymers according to the resent invention such as in particular TILAMAR® Fix A1000 can also be easily combined with other commercially available hair styling polymers in order to further improve the performance. Some basic formulation examples are given in the following part without being limited thereto.

8.1. Combination with Hair Styling Polymers Available at Dow:

The given concentrations are examples and could be varied according to requirements in ranges of 1-10%.

| Ingredients | INCI Name | A | B | C |
|---|---|---|---|---|
|  |  | wt.-% | | |
| ALCOHOL DENAT. | Alcohol denat. | Ad. 100 | | |
| Polymer Beads according to the invention, in particular TILAMAR ® Fix A1000 | Acrylates Copolymer | 5.00 | | |
| ACUDYNE ™ DHR | Acrylates/Hydroxyesters acrylates Copolymer | 2.65 | — | — |
| ACUDYNE ™ LT-120 | Acrylates/C 1-2 Succinates/Hydroxyacrylates Copolymer | — | 2.65 | — |
| ACUDYNE ™ 180 | Acrylates/Hydroxyesters acrylates Copolymer | — | — | 2.65 |
| AMP Ultra PC 2000 | Aminomethyl Propanol | 1.30 | 1.34 | 1.32 |
| D-PANTHENOL | Panthenol | 0.15 | 0.15 | 0.15 |
| DOW CORNING 193 | PEG-12 Dimethicone | 0.15 | 0.15 | 0.15 |

8.2. Combination with Hair Styling Polymers Available at BASF: The given concentrations are examples and could be varied according to requirements in ranges of 1-10%.

| Ingredients | INCI Name | 1 | 2 | 3 | 4 | 5 | 6 | 7 |
|---|---|---|---|---|---|---|---|---|
|  |  | wt.-% | | | | | | |
| ALCOHOL DENAT. | Alcohol denat. | Ad 100 | | | | | | |
| Polymer Beads according to the invention, in particular TILAMAR ® Fix A1000 | Acrylates Copolymer | 5.0 | | | | | | |
| LUVIMER ® P100 | Acrylates Copolymer | 1.2 | | | | | | |
| LUVIMER ® PRO 55 | Acrylates Copolymer |  | 3.25 | | | | | |
| LUVISKOL ® VA 37E | VP/VA Copolymer |  |  | 2.4 | | | | |
| LUVISKOL ® PLUS | Polyvinylcaprolactam |  |  |  | 3.0 | | | |
| LUVISET ® CAN | VA/Crotonates/Vinyl neodecanoate Copolymer |  |  |  |  | 1.2 | | |
| LUVISET ® CA 66 | Vinyl acetate/Crotonic acid copolymer |  |  |  |  |  | 1.2 | |
| LUVISET ® SHAPE | Polyacrylate-22 |  |  |  |  |  |  | 3.45 |
| AMP Ultra PC 2000 | Aminomethyl Propanol | Ad. to 90-100% neutralisation level of polymers | | | | | | |
| D-PANTHENOL | Panthenol | 0.15 | | | | | | |
| DOW CORNING 193 | PEG-12 Dimethicone | 0.15 | | | | | | |

8.2. Continued

The given concentrations are examples and could be varied according to requirements in ranges of 1-10%.

| Ingredients | INCI Name | 8 | 9 | 10 | 11 | 12 | 13 |
|---|---|---|---|---|---|---|---|
| | | | | wt.-% | | | |
| ALCOHOL DENAT. | Alcohol denat. | | | Ad 100 | | | |
| Polymer Beads according to the invention, in particular TILAMAR ® Fix A1000 | Acrylates Copolymer | | | 5.0 | | | |
| LUVISKOL ® VA 55 I | VP/VA Copolymer (and) Isopropanol | 2.4 | | | | | |
| LUVISKOL ® VA 37 I | VP/VA Copolymer (and) Isopropanol | | 2.4 | | | | |
| ULTRAHOLD ® 8 | Acrylate/acrylamide Copolymer | | | 1.2 | | | |
| ULTRAHOLD ® STRONG | Acrylates/t-Butyl-acrylamide copolymer | | | | 1.2 | | |
| LUVISET ® PUR | Polyurethane-1 | | | | | 4 | |
| LUVIFLEX ® SILK | PEG/PPG 25/25 Dimethicone/Acrylates copolymer | | | | | | 2.4 |
| AMP Ultra PC 2000 | Aminomethyl Propanol | Ad. to 90-100% neutralisation level of polymers | | | | | |
| D-PANTHENOL | Panthenol | | | 0.15 | | | |
| DOW CORNING 193 | PEG-12 Dimethicone | | | 0.15 | | | |

8.3 Combination with Hair Styling Polymers Available at Akzonobel:

The given concentrations are examples and could be varied according to requirements in ranges of 1-10%.

| PRODUCT NAME | INCI Name | 1 | 2 | 3 | 4 | 5 | 6 | 7 | 8 | 9 |
|---|---|---|---|---|---|---|---|---|---|---|
| | | | | | | wt.-% | | | | |
| ALCOHOL DENAT. | Alcohol denat. | | | | | Ad 100 | | | | |
| Polymer Beads according to the invention, in particular TILAMAR ® Fix A1000 | Acrylates Copolymer | | | | | 5.0 | | | | |
| AMPHOMER | Octylacrylamide/acrylates/butylaminoethyl methacrylate copolymer | 1.2 | | | | | | | | |
| AMPHOMER LV-71 | Octylacrylamide/acrylates/butylaminoethyl methacrylate copolymer | | 1.2 | | | | | | | |
| AMPHOMER 4961 | Acrylates/octylacrylamide copolymer | | | 1.2 | | | | | | |
| AMPHOMER HC | Acrylates/octylacrylamide copolymer | | | | 1.2 | | | | | |
| RESYN 28-2930 | VA/crotonates/vinyl neodecanoate copolymer | | | | | 1.2 | | | | |
| RESYN XP | Acrylates/octylacrylamide copolymer | | | | | | 1.2 | | | |
| BALANCE 47 | Octylacrylamide/acrylates/butylaminoethyl methacrylate copolymer | | | | | | | 1.2 | | |
| BALANCE CR | Acrylates copolymer | | | | | | | | 2.4 | |
| DYNAMX ® | Polyurethane-14 (and) AMP-acrylates copolymer | | | | | | | | | 4 |
| AMP Ultra PC 2000 | Aminomethyl Propanol | Ad. to 90-100% neutralization level of polymers | | | | | | | | |
| D-PANTHENOL | Panthenol | | | | | 0.15 | | | | |
| DOW CORNING 193 | PEG-12 Dimethicone | | | | | 0.15 | | | | |

8.4 Combination with Hair Styling Polymers Available at Lubrizol:

The given concentrations are examples and could be varied according to requirements in ranges of 1-10%.

| Ingredients | INCI Name | A wt.-% | B wt.-% |
|---|---|---|---|
| ALCOHOL DENAT. | Alcohol denat. | Ad 100 | Ad 100 |
| Polymer Beads according to the invention, in particular TILAMAR® Fix A1000 | Acrylates Copolymer | 5.00 | |
| Fixate™ G-100 Polymer | AMP-Acrylates/Allyl Methacrylate Copolymer | 8.00 | — |
| Fixate™ Superhold Polymer | Polyacrylate-2 Crosspolymer | — | 5.00 |
| AMP Ultra PC 2000 | Aminomethyl Propanol | Ad. to 90-100% neutralization level of polymers | Ad. to 90-100% neutralization level of polymers |
| D-PANTHENOL | Panthenol | 0.15 | 0.15 |
| DOW CORNING 193 | PEG-12 Dimethicone | 0.15 | 0.15 |

The invention claimed is:

1. A process for the preparation of acrylic polymers beads comprising:
    (a) providing a monomer composition consisting of a mixture of 10-30 wt. % methacrylic acid (MAA), 35-65 wt. % n-butyl methacrylate (BMA), 5-15 wt. % ethylacrylate (EA) and 10-35 wt. % ethyl methacrylate (EMA), wherein the EMA and EA are present in amounts to achieve a coefficient of EMA to EA (w/w) in a range of 4 to 1, and
    (b) subjecting the monomer composition to suspension polymerization to obtain acrylic polymer beads having an average diameter of between 50 and 1500 µm and a residual monomer content of less than 250 ppm.

2. The process according to claim 1, wherein the monomer composition consists of a mixture of 17-22 wt.-% of the MMA, 44-56 wt.-% of the BMA, 9-15 wt.-% of the EA, and 15-25 wt.-% of the EMA.

3. The process according to claim 1, wherein the coefficient of EMA to EA (w/w) is in the range of 2.0 to 1.3.

4. The process according to claim 3, wherein the MMA is present in the monomer composition in an amount of 15-22 wt.-%.

5. The process according to claim 1, wherein the process further comprises isolating the acrylic polymer beads followed drying the bead in a drying step at 40-100° C.

6. The process according to claim 5, wherein the drying step is carried out over a period of 3 to 40 hours.

7. The process according to claim 5, comprising drying the bead in the drying step at 80 to 100° C.

8. Acrylic polymer beads obtained by the process according to claim 1.

9. The acrylic polymer beads according to claim 8, wherein the residual monomer content of the acrylic beads is less than 100 ppm.

10. A cosmetic composition comprising the acrylic polymer beads according to claim 8, and a cosmetically acceptable carrier.

11. The cosmetic composition according to claim 10, wherein the composition comprises the acrylic polymer beads in an amount of 0.01-20 wt.-%, based on the total weight of the cosmetic composition.

12. The cosmetic composition according to claim 10, wherein the composition comprises the acrylic polymer beads in an amount of 0.05-10 wt.-%, based on the total weight of the cosmetic composition.

13. A hair styling preparation which comprises the cosmetic composition according to claim 12.

14. The hair styling preparation according to claim 13, which is in the form of a styling cream, styling gel, liquid hair-setting preparation, hair foams or hairspray.

15. The hair styling preparation according to claim 13, which is an aerosol hairspray.

16. The hair styling preparation according to claim 13, which further comprises at least one additional hair fixative resin.

* * * * *